US009187575B2

(12) United States Patent
Sauter et al.

(10) Patent No.: US 9,187,575 B2
(45) Date of Patent: Nov. 17, 2015

(54) ISOLATION OF GLUCAN PARTICLES AND USES THEREOF

(75) Inventors: Martin Sauter, Herznach (CH); Stefan Freimund, Zürich (CH); Hans Dutler, Zürich (CH); Othmar Käppeli, Würenlos (CH); Ahmad Al-Ghazawi, Waltham Cross (GB); Eugen Schwarz, Bensheim (DE); Lutz Thomas, Wolfenbüttel (DE); Helmut Schöberl, Darmstadt (DE)

(73) Assignee: ABAC R&D AG, Wallisellen (CH)

( * ) Notice: Subject to any disclaimer, the term of this patent is extended or adjusted under 35 U.S.C. 154(b) by 1988 days.

(21) Appl. No.: 11/293,467

(22) Filed: Dec. 2, 2005

(65) Prior Publication Data

US 2006/0134759 A1  Jun. 22, 2006

Related U.S. Application Data

(63) Continuation of application No. 10/343,604, filed as application No. PCT/EP01/08851 on Jul. 31, 2001, now abandoned.

(30) Foreign Application Priority Data

Aug. 3, 2000 (EP) ..................................... 00116764

(51) Int. Cl.
| | | |
|---|---|---|
| *C12P 19/04* | (2006.01) | |
| *C08B 37/00* | (2006.01) | |
| *A23K 1/16* | (2006.01) | |
| *A23L 1/054* | (2006.01) | |
| *A61K 8/73* | (2006.01) | |
| *A61Q 19/00* | (2006.01) | |
| *B01J 20/26* | (2006.01) | |

(52) U.S. Cl.
CPC ........... *C08B 37/0024* (2013.01); *A23K 1/1643* (2013.01); *A23L 1/0543* (2013.01); *A61K 8/73* (2013.01); *A61Q 19/00* (2013.01); *B01J 20/26* (2013.01); *A61K 2800/412* (2013.01); *B01J 2220/52* (2013.01)

(58) Field of Classification Search
USPC ......................................... 536/55.1; 435/101
See application file for complete search history.

(56) References Cited

U.S. PATENT DOCUMENTS

| | | | |
|---|---|---|---|
| 3,867,554 A | | 2/1975 | Sucher et al. |
| 3,880,742 A | | 4/1975 | Jamas et al. |
| 4,143,201 A | * | 3/1979 | Miyashiro et al. ............ 428/403 |
| 4,454,315 A | | 6/1984 | Sasaki et al. |
| 4,707,471 A | | 11/1987 | Larm et al. |
| 4,795,653 A | | 1/1989 | Bommarito |
| 4,810,646 A | * | 3/1989 | Jamas et al. ................. 435/101 |
| 4,962,094 A | | 10/1990 | Jamas et al. |
| 4,992,540 A | | 2/1991 | Jamas et al. |
| 5,028,703 A | | 7/1991 | Jamas et al. |
| 5,037,972 A | | 8/1991 | Jamas et al. |
| 5,082,936 A | | 1/1992 | Jamas et al. |
| 5,250,436 A | | 10/1993 | Jamas et al. |
| 5,506,124 A | | 4/1996 | Jamas et al. |
| 5,576,015 A | | 11/1996 | Donzis |
| 5,705,184 A | | 1/1998 | Donzis |
| 6,020,324 A | * | 2/2000 | Jamas et al. .................... 514/54 |
| 6,045,834 A | * | 4/2000 | Howes et al. .................... 426/2 |
| 6,143,731 A | | 11/2000 | Jamas et al. |

FOREIGN PATENT DOCUMENTS

| | | |
|---|---|---|
| EP | 0 440 725 B1 | 10/1989 |
| EP | 0 416 343 A2 | 3/1994 |
| EP | 0790316 | 8/1997 |
| JP | 55-709 | 1/1980 |
| JP | 60-196195 | 10/1985 |
| JP | 62-40262 | 2/1987 |
| WO | WO 91/07091 A1 | 5/1991 |
| WO | WO 92/07064 | 4/1992 |
| WO | WO 94/03500 | 2/1994 |
| WO | WO 94/03500 A1 | 2/1994 |
| WO | WO 94/04163 | 3/1994 |
| WO | WO 96/28476 | 9/1996 |

OTHER PUBLICATIONS

Scaringi et al J. General Microbiology, 1988, 134, 165-74.*
Yan et al, Expert Opin. Biol. Ther. 2005, 5(5), 691-702.*
R. Bonaly et al., "Etude des Parois de Levures du Genre Rhodotorula", *Biochim. Biophy. Acta*, 244:484-494 (1971), Elsevier Science, Oxford, United Kingdom.
J.S.D. Bacon et al., "The Glucan Components of the Cell Wall of Baker's Yeast (*Saccharomyces cerevisiae*) Considered in Relation to its Ultrastructure", *Biochem. J.* 114:557-567 (1969), Portland Press, London, England.
C.E. Ballou, "Structure and Biosynthesis of the Mannan Component of the Yeast Cell Envelope", *Adv. Microbiol. Physiol.*, 14:93-158 (1976), Academic Press, London, England.
R. Sentandreu et al., "The Structure of a Glycopeptide Isolated from the Yeast Cell Wall", *Biochem. J.*, 109:419-432 (1968), Portland Press, London, England.
R. Sentandreu et al., "The Characterization of Oligosaccharides Attached to Threonine and Serine in a Mannan Glycopeptide Obtained from the Cell Wall of Yeast", *Carbohydr. Res.*, 10:584-585 (1969), Elsevier Science B.V., Amsterdam, Holland.
C.E. Ballou, "Some Aspects of the Structure, Immunochemistry, and Genetic Control of Yeast Mannas", *Adv. Enzymol.*, 40:239-270 (1974), Wiley Interscience, New York, NY USA.
S. Peat et al., "Polysaccharides of Baker's Yeast. Part III. The Presence of 1:6-Linkages in Yeast Glucan", *J. Chem. Soc.*, 3868-3870 (1958), Chemical Society (Gt Britain), London, England.
G.H. Fleet et al., "Isolation and Composition of an Alkali-Soluble Glucan from the Cell Walls of *Saccharomyces cerevisiae*", *J. Gen. Microbiol.*, 94:180-192 (1976), Reading Society for General Microbiology, Reading, England.
M. Kopecka, "Electron Microscopic Study of Purified Polysaccharide Components Glucans and Mannan of the Cell Walls in the Yeast *Saccharomyces cerevisiae*", *J. Basic Microbiol.*, 25:161-174 (1985), Akademie Verlag, Berlin, Germany.

(Continued)

*Primary Examiner* — Ganapathy Krishnan
(74) *Attorney, Agent, or Firm* — Buchanan Ingersoll & Rooney PC

(57) ABSTRACT

The present invention relates to the isolation of novel glucan particles but also to mannoprotein from natural sources such as yeast cell walls, novel isolation methods, and the use of products thereof.

21 Claims, 8 Drawing Sheets

(56) References Cited

OTHER PUBLICATIONS

E. Cabib et al., "Chitin and Yeast Budding", *Journal of Biological Chemistry*, 246:152-159 (1971), American Society for Biochemistry and Molecular Biology, Baltimore, MD, USA.

P. Jung et al., "Identification of the Lipid Intermediate in Yeast Mannan Biosynthesis", *Eur. J. Biochem*, 37:1-6 (1973), Blackwell Science, Berlin, Germany.

F.M. Klis, "Review: Cell Wall Assembly in Yeast", *Yeast* 10:851-869 (1994), Wiley, Chicester, England and New York.

D.L. Williams et al, "A Method for the Solubilization of a (1 → 3)-β -D-glucan Isolated from *Saccharomyces cerevisiae*", *Carbohydrate Research*, 219:203-213 (1991), Elsevier Science Publishers B.V., Amsterdam.

T. Nakajima et al., "Characterization of the Carbohydrate Fragments Obtained from *Saccharomyces cerevisiae* Mannan by Alkaline Degradation", *J. Biol. Chem*. 249:7679-7684 (1974), American Society for Biochemistry and Molecular Biology, MD USA.

E. Valentin et al., "Solubilization and Analysis of Mannoprotein Molecules from the Cell Wall of *Saccharomyces cerevisiae*", *J. General Microbiol*., 130:1419-1428 (1984), Reading Society for General Microbiology, Reading, England.

F.I.J. Pastor et al, "Structure of the *Saccharomyces cerevisiae* Cell Wall, Mannoproteins Released by Zmolyase and Their Contribution to Wall Architecture", *Biochimica et Biophysica Acta*, 802:292-300 (1984), Elsevier, Amsterdam, Holland.

S. Peat et al., "Polysaccharides of Baker's Yeast. Part IV. Mannan", *J. Chem. Soc.* 29-34 (1961), Chemical Society (Gt Britain), London, England.

N. Shibata et al., "Immunochemical Properties of Mannan-Protein Complex Isolated from Viable Cells of *Saccharomyces cerevisiae* 4484-24D-1 Mutant Strain by the Action of Zymolyase", *Microbiol. Immunol*., 28(12):1283-1292 (1984), Springer Verlag, Berlin Germany and New York.

Y. Okubo et al., "Relationship Between Phosphate Content and Immunochemical Properties of Subfractions of Bakers' Yeast Manna", *J. of Bacteriology*, 136:63-68 (1978), American Society for Microbiology, Washington, DC, USA.

D.L. Williams et al., "Molecular Weight Analysis of a Water-Insoluble, Yeast-Derived (1 → 3)-β -D-glucan by Organic-Phase Size-Exclusion Chromatography", *Carbohydrate Research* 253:293-298 (1994), Elsevier Science B.V., Amsterdam, Holland.

L. Scaringi et al., "Cell Wall Components of *Candida Albicans* as Immunomodulators: Induction of Natural Killer and Macrophage-mediated Peritoneal Cell Cytotoxicity in Mice by Mannoprotein and Glucan Fractions", *J. of General Microbiology*, 134:1265-1274 (1988), Reading Society for General Microbiology, Reading, England.

Cassone, A. et al., Journal of General Microbiology, 1978, 105, 263-273.

Scaringi, L. et al., J. General Microbiology, 1988, 134, 1265-74.

International Search Report, PCT/EP01/08851.

Bacon et al., "The Glucan Components of the Cell Wall of Baker's Yeast (*Saccharomyces cerevisiae*) Considered in Relation to its Ultrastructure," *Biochem J.*, 1969, pp. 557-567, vol. 114, Great Britain.

Klis et al., "Dynamics of cell wall structure in *Saccharomyces cerevisiae*," *FEMS Microbiology Reviews*, 2002, pp. 239-256, vol. 26, Elsevier Science B.V.

Manners et al., "The Structure of a β-(1→3)-D-Glucan from Yeast Cell Walls," *Biochem. J.*, 1973, pp. 19-30, vol. 135, Great Britain.

Nguyen et al., "Composition of the cell walls of several yeast species," Appl Microbiol Biotechnol (1998), 50: pp. 206-212.

* cited by examiner

Basic steps for glucan particle preparation from yeast

Electronmicrograph of the surface of a glucan particle according
To Example 2b, acetone-treated sample; side length 1.08 μm.

Confocal fluorescence microscopy image of lipid-containing Glucan particles according to Example 2b.

Confocal fluorescence microscopy image after cosslinking And carboxymethylation of acetone-treated glucan particles according to Example 2b.

$^{13}$C NMR spectrum of mannoprotein according to Example 1 in D$_2$O.

$^1$H NMR spectrum of acetone-treated glucan particles according to Example 2b in $D_6$-DMSO.

$^{13}$C NMR spectrum of acetone-treated glucan particles according to Example 2b in $D_6$-DMSO.

ISOLATION OF GLUCAN PARTICLES AND USES THEREOF

CROSS REFERENCE TO RELATED APPLICATIONS

This application is a continuation application that claims the benefit of priority of U.S. Utility patent application Ser. No. 10/343,604, filed on Aug. 4, 2003 now abandoned, as the United States national phase under 35 U.S.C. §371 of International Application No. PCT/EP01/08851, filed on Jul. 31, 2001, designating the United States, and claiming priority to Application No. EP 00116764.2, filed on Aug. 3, 2000. All of the foregoing applications are incorporated by reference herein.

FIELD OF INVENTION

The present invention relates to the isolation of novel glucan particles from natural sources such as yeast cell walls, novel isolation methods, and the use of products.

BACKGROUND OF THE INVENTION

The cell walls of unicellular organisms and of plants mainly consist of polsaccharides, partly associated with proteins. Important functions are: Rigidity, physical protection of the cells, osmotic stability, selective permeability support, cell/cell adhesion, binding of compounds and extracellular enzyme support. Since the polysaccharides form a three dimensional network, cell walls may serve as a resource for particles that maintain certain useful properties of the native cell wall such as selective adsorption capacity. The final properties of the particles depend on the starting material (e.g. yeast strain or other microbial or plant cells) and on the level of preservation of the structural integrity during isolation.

Therefore, a prerequisite for the isolation of functional particles are non-denaturing isolation procedures.

In the following the structure and composition of the yeast cell wall, an important potential resource of said particles, is outlined.

The precise structure and composition of the yeast cell wall strongly depends on the type of yeast strain and culture conditions (R. Bonaly, H. Moulki, A Touimi Benjellouen, M. Pierrefitte, Biochhn. Biophys Acta 244,484 (1971)). A shortage of amino acids, for example, reduces the protein content in the cell wall. Yeasts are unicellular organisms with a rigid cell wall made of polysaccharides. The cell shape is oval to round with an average diameter of 5-13 μm. The cell walls show a thickness of about 70 nm and account for 15-25% of the yeast dry weight (J. S. D. Bacon, V. C. Farmer, D. Jones, I. F. Taylor, Biochem J. 114,557 (1969)). As mentioned, the overall composition of the cell wall varies and depends on the special strain and on culture conditions. This forms the basis for the isolation of a great number of cell wall particles with different properties.

In general, the main components of the yeast cell wall are mannan (typically about 30% by weight), glucan (also about 30% by weight), protein (15% by weight), lipids (about 10% by weight) and chitin (about 2% by dry weight). The latter is exclusively located in the budding scar of the yeasts.

The Mannoprotein Component

By definition mannan, is a polymer that is exclusively composed of mannose units. In yeasts, mannan is associated with protein in both, the external surface of the yeast cell wall, as a muscigenous polysaccharide and in the inner cell membrane. It accounts for 20-50% of the dry weight (C. E. Ballou, Adv. Microbiol. Physiol. 14, 93 (1976). Mannan is linked to a core-peptide chain as an oligomer or polymer (R. Sentandreu, D. H. Northcote, Biochem J. 109,419 (1968)). The complex consists of 5-50% proteins. Oligomeric mannan is bonded directly to serine and threonine (R. Santandreu, D. H. Northcote, Carbohydr. Res. 10, 584 (1969)) whereas polymeric mannan is bonded to aspargine via N-acetylglucosamine. The many individual aspects relating to the mannoprotein complex, including that the mannose units are linked by α-1,6, α-1,2 and α-1,3-linkages were compiled and reviewed by Ballou et al. (C. E. Ballou, Adv. Microbiol. Physiol. 14, 93 (1976); C. E. Ballou, Adv. Enzymol. 40, 239 (1974)).

The Glucan Component

Glucan is a glucose polymer and accounts for 30-60% of the dry weight. The majority of the polyglucoside is linked via β-1,3 glycosidic linkages and only 10-20% by β-1,6 glycosidic linkages (S. Peat, J. R. Turvey, J. M. Evans, J. Chem. Soc. 3868 (1958)). If glucan is treated with approximately 3% caustic soda at 75° C., a maximum of one-third of the glucan is solubilized (J. S. Bacon, V. C. Farmer, D. Jones, Biochem. J. 114, 557(1969)). Consequently the glucan is divided into (1) an alkali insoluble fraction (glucan A), and (2) an alkali soluble fraction (glucan B) (G. H. Fleet, D. J. Manners, J. Gem Microbiol. 94, 180 (1976)).

Glucan A accounts for 80-85% of the cell wall glucan and consists primarily of β-1,3, glycosidic linkages as well as of about 3% β-1,6 glycosidic linkages. 80-85% of the glycosidic linkages of glucan B (15-20% of the total glucan) are β-1,3 and 8-12% are β-1,6 glycosidic linkages 3-4% of the glucose units are branchings. The β-1,6 glycosidic linkages are selectively hydrolysed by acetylosis. It is proposed that the β-1,3 glucan chains are linked via β-1,6 intermediate chains (J. S. D. Bacon, V. O. Farmer, D. Jones, Biochem. J. 114, 557 (1969)). Using electron microscopy it was possible to demonstrate a fibrillar structure for the β-1,3 component and an amorphous structure of the 1,6 component (M. Kopecká, J. Basic Microbial. 25,161 (1985)).

Chitin and Lipid Components

Chittin (N-acylated poly-glucosamine) is located exclusively in the budding scars, where it forms a ring (E. Cabib, B. Browers, J. Biol. Chem. 246, 152 (1971)). As a lipid compound dolichol phosphate was isolated from the cell walls (P. Jung, W. Tanner, Eur. J. Biochem. 37, 1 (1973)). The rest of the lipid component consists of glycerol esters of various fatty acids.

The Structure of the Yeast Cell Wall

Electron microscopic investigation of the process of biosynthesis and assembly of the glucans in *Candida albicans* reveals the development of the fibrous network of the cell wall. The triple helices which appear as microfibrils with a diameter of approx. 2 nm are self-assembled end-to-end and side by side and are twisted together leading to fibrils of 4-8 nm in diameter. These fibrils finally associate to flat ribbon-shaped bundles, 8-16 nm thick and 100-200 nm wide and thus form the basic network structure of the cell wall. The interfibrillar spaces of the network at this stage have dimensions of about 100-200 nm and most likely mark the origin of the pores which are present in the cell wall at the final stage and which constitute the structural basis for their ability to adsorb compounds with great significance in a large number of different areas. They are gradually filled with the additional components and manno-proteins which are known to form anchors to the membrane lipids.

Isolation of Yeast Cell Wall Components

Fractionation of the cell walls, as e.g. of *Saccharomyces cerevisiae* starts either from whole cells or from cell walls e.g.

obtained by autolysis; both starting materials may be used in dry or wet form. In some cases the cells or cell walls are pre-treated mechanically (by sonification or by treatment with glass beads). The starting material as well as the mechanical disruption greatly influence the purity of the resulting fraction. A large number of different methods were reported for the isolation of cell wall components (F. M. Klis, Yeast 10, 851 (1994)). They can be grouped (1) in methods for the isolation of mannoprotein, and (2) in methods for the isolation of glucan.

A common reagent of chemical methods for the isolation of mannoprotein is sodium hydroxide of varying concentrations and using a wide range of temperatures and treatment times (Int. Patent WO 94/04163 (1994); D. L. Williams, R. B. McNamee, E. L. Jones, H A. Pretus, H. E. Ensley, I. Williams, N. R. DiLuzio, Carbohydr. Res. 219, 203 (1991)). Depending on the reaction conditions, such treatments also solubilize more or less glucan (see above definition of soluble and insoluble glucan), In some cases, organic bases like ethylene diamine and buffers like citrate salts find application to solubilize mannoproteins (R. Sentandreu, D. H. Northcote, Biochem. J. 109, 419 (1968); T. Nakajima, C. Ballou, J. Biol. Chem. 249, 7679 (1974)). Extraction with a 2% boiling sodium-dodecyl-sulfate (SDS) in the presence or absence of reducing agents, like mercaptoethanol, represents a widely used approach to free gluten from mannoproteins and other proteins (E. Valentin, E. Herrero, F. I. J. Pastor, R. Sentandreu, J. General Microbiol. 130, 1419 (1984); F. I. J. Pastor, E. Valentin, E. Herrero, R. Sentandreu, Biophys. Acta 802, 292 (1984)). Treatment of whole cells with pure water at temperatures of up to 135° C. was also applied, yielding a highly contaminated mannoprotein fraction (S. Peat, W. J. Whelan, T. E. Edwards, J. Chem. Soc. 29 (1961); N. Shibata, K. Mizugami, S. Susuki, Microbiol. Immunol. 28, 1283 (1984); Y. Okubo, T. Ichikawa, S Susuki, J. Bact. 136, 63 (1978)).

Enzymatic methods were alternatively used for releasing the manno-proteins. For this purpose, proteases and glucanases are used, acting on the protein part of the mannan or the glucan fixing the mannoprotein (β-1,6 glucan).

The mannan-free glucan is further purified by procedures that include acid treatment such as acetic acid or HCI.

The summarized chemical procedures for isolation and purification of cell wall components will more or less affect the nativity of the polymers, which is primarily reflected in the occurrence of increased amounts of soluble glucan and in a disturbance of the structure of the insoluble glucan fraction. It is especially the latter negative impact of existing glucan isolation procedures that make the insoluble glucan less suitable for adsorbent applications. When such chemical treatments are used under milder conditions, the pores of the glucan skeleton are not properly activated, i.e. freed from physically or chemically bound pore filling material. This also yields insoluble glucan not optimal for adsorption.

SUMMARY OF THE INVENTION

Therefore, it is the objective of this invention to provide simple and effective methods for the isolation of glucan particles, which are characterised by a native structure and active pores.

The respective process for isolating glucan particles with such features from cells, cell walls, or cell wall fragments of unicellular organisms like yeasts or fungi or of cell wall residues of glucan-containing plants, comprises the steps a)-c) which may be proceeded in any sequence (FIG. 1).

These steps are characterised as follows:
 a) extracting mannoproteins with water at temperatures above the boiling point of water from suspensions,
 b) removal of contaminating proteins with protease or non-denaturing chemical means,
 c) removal of contaminating lipids with lipases or by solvent extraction.

The extraction of step is preferably proceeded with adjusted pH under elevated pressure.

Depending on the starting material one or more steps may be deleted. Cells, cell walls or cell wall fragments of e.g. yeast or fungi or of unicellular organisms other than yeast or cell wall residues of glucan-containing plant tissues are used as starting material.

According to the invention these new glucan particles are obtainable from these starting materials by combining steps c) and b) or steps b) and c) respectively.

As far as appropriate, residual non-glucan components may be removed by non-denaturing chemical means, such as extraction of non-glucan residues with NaOH at low concentration and temperature, with 2% sodium dodecylsulfate solution at elevated temperature, and with organic solvents, such as acetone, at room temperature or at elevated temperatures.

If useful starting materials are treated according to the invention and if the steps of the inventive process are carried out in a suitable sequence the basic structure of the isolated glucan particles remains intact and shows properly active pores. Naturally this means that each single step of the process has to be adapted to the treated material.

DETAILED DESCRIPTION OF THE INVENTION

Figure 1:
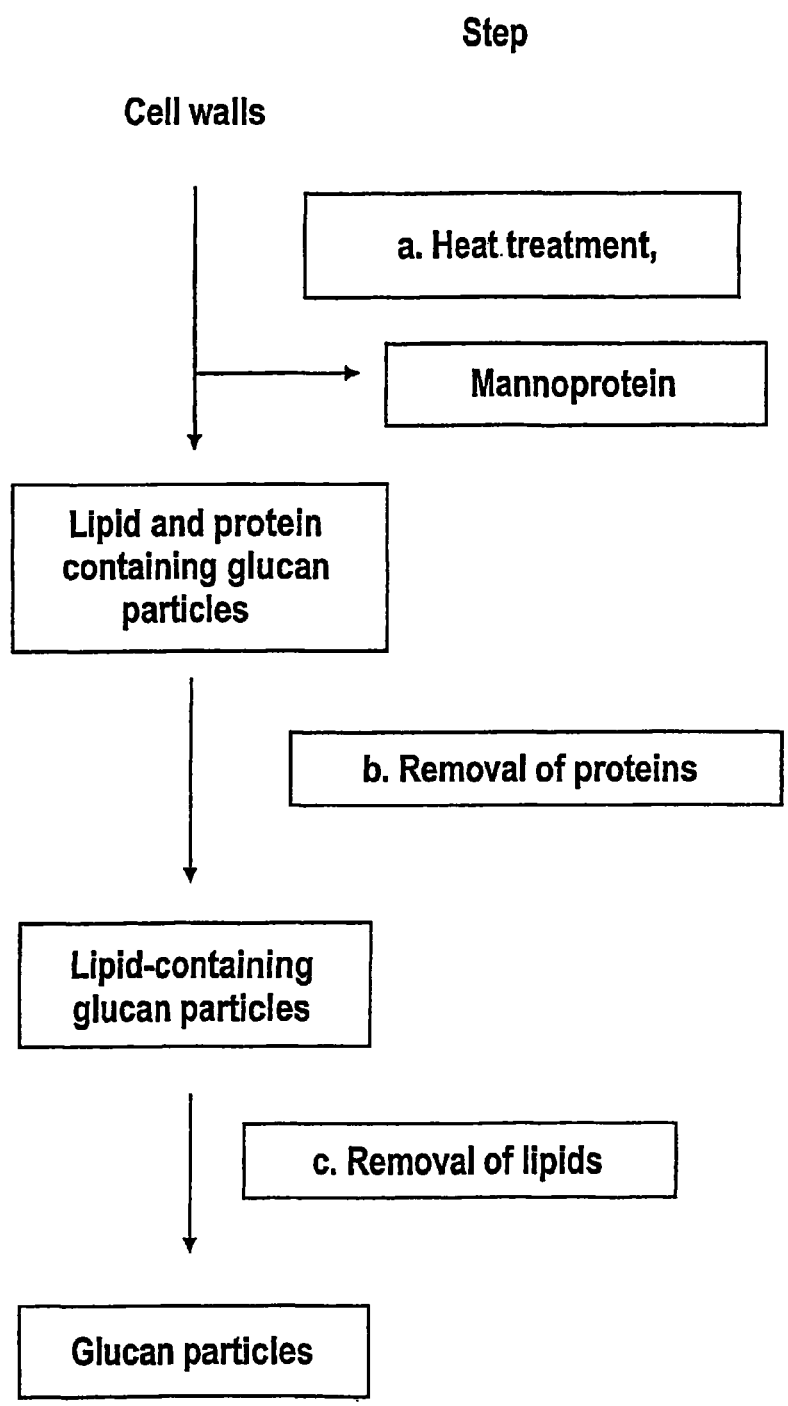
FIG. 1 presents basic steps for glucan particle preparation from yeast.

It has been found that glucan particles can be isolated with preserved porous and fibrous structural properties. These particles are having a molecular weight ($M_w$ or $M_n$) of more than 100 000, especially more than 400,000, having essentially retained its native structure after solubilization by carboxymethylation. Their particle sizes are in a range of 0.1 to 25 micrometers, preferably 0.5 to 15 micrometers, and most preferably 2 to 10 micrometers. In contrast to known glucan these glucan particles are insoluble in water and in most of the known organic solvents, while they are having activated pores and are showing an increased stability at high pH-values.

Additionally, these glucan particles are able to form stable gels; for example they are forming a stable gel in organic solvents or acidified water, when an aqueous suspension of these particles is heated to a temperature higher than 80° C.

Glucan particles according to the present invention may be obtained by extracting mannoproteins from an aqueous cell wall suspension in the concentration range of 1-20% by weight, preferably 10-20%, most preferably 13-17% with adjusted pH in the range of 5-9, preferably pH 6-8, most preferably pH 6.5 to 7.5, at a temperature in the range of 100-150° C., preferably 110-140° C., most preferably 120-130° C. for a defined period of time, e.g. 3-7 hours, under elevated pressure.

According to the described treatment lipid and protein containing glucan particles are obtained as solid fraction and mannoprotein as the soluble fraction, which may be isolated.

The extracted mannoprotein can be isolated from the aqueous solution by precipitation. It is found, that this precipitation can be induced by mixing the solution with an alcohol. Suitable alcohols are short chained alcohols. Preferably an alcohol selected from the group methanol, ethanol, propanol or butanol is used. Most preferably the precipitation is carried out with ethanol. Alternatively the mannoprotein may be concentrated by ultra-filtration before precipitation with alcohols.

Lipid and protein containing glucan particles, removed by centrifugation or filtration, are subsequently treated with a protease at pH values and temperatures required for optimum protease activity for 1-12 hours, preferably 3-8 hours and most preferably 4-6 hours. Lipid containing glucan particles result from this treatment and can be isolated.

For obtaining intact mannoprotein the protease treatment on the glucan particles has to be done after the mannoprotein fraction has been separated.

Lipid containing glucan particles removed by centrifugation or filtration, are subsequently treated with a lipase at pH values and temperatures required for optimum protease activity for 1-12 hours, preferably 1-5 hours and most preferably 2-4 hours. From the treatment glucan particles result and may be isolated.

Alternatively lipid containing glucan particles may be obtained from lipid and protein containing glucan particles by extraction of protein containing contaminants either with aqueous alkaline solutions such as earth alkali hydroxide, like NaOH, sodium carbonate and sodium hydrogen carbonate solutions at low concentration and low temperature or with sodium dodecylsulfate at a concentration in the range of 0.1-5% by weight, preferably 1-3% by weight, most preferably 1.5 to 2.5% by weight.

Glucan particles may alternatively be obtained from lipid containing glucan particles by cold or hot organic solvent extraction with solvents that are miscible with water, e.g. selected from the group acetone, ethanol, methanol, isopropanol and butanol or mixtures thereof, or with solvents that are not miscible with water, e.g. selected from the group dialkylketones, e.g. isobutylmethylketone, hydrocarbons, e.g., hexane, chlorinated hydrocarbons, e.g. chloroform, methylenchloride, tetrachloroethylene and ester solvents, e.g. ethylacetate, or mixtures thereof, or with mixtures of organic solvents that are miscible with water with organic solvents that are not miscible with water, e.g. methanol/chloroform in a ration of volume of 1:1 or hexane/isopropanol in a ration of volume of 3:2; or with supercritical fluids, e.g. supercritical $CO_2$; or with supercritical $CO_2$ and organic solvents as modifiers.

Therefore, the process for isolating insoluble native glucan particles with properly activated pores from cells, cell walls, or cell wall fragments of unicellular organisms like yeast or fungi or of cell wall residues of glucan-containing plants, comprises the steps a)-c) mentioned above which may be proceeded in any sequence. These steps are characterised as follows:

a) extracting mannoproteins with water at temperatures above the boiling point of water from suspensions with adjusted pH under elevated pressure, b) treatment with proteases after pH adjustment at high level and removal of proteins, c) treatment with lipases after pH adjustment at high level and removal of contaminating lipids, or if appropriate by solvent extraction.

Optionally non-glucan residues can be removed by non-denaturing chemical means and as already said above depending on the starting material one or more steps may be deleted.

Thus glucan particles are prepared which are insoluble in water and most of the common solvents, especially most of the common organic solvents. A unique advantage is their stable three-dimensional structure, which is nearly unchanged in the presence of adsorbed substances or if their surface reacts with active groups. The particles according to the invention possess activated open pores.

A valuable by-product of the present process, a mannoprotein, which may be recovered from step a) of the process. For this purpose the recovered aqueous fraction of step a) is added to and mixed with an alcohol This alcohol may be a short-chained alcohol, especially one of the group methanol, ethanol, propanol and butanol. The extracted mannoprotein may be recovered after precipitation by cooling for several hours.

Distinguishing properties of glucan particles isolated according to the present invention are also:

1. Solubility in DMSO

Glucan particles according to the invention swell markedly in DMSO but can easily be centrifuged which means that they are not truly dissolved. For comparisons, glucan particles isolated by harsh conditions (conventional glucans) dissolve in DMSO (e.g. D. L. Williams, H. A. Pretus, H. E. Ensley, I. W. Browder, Carbohydr Res. 253,293 (1994)) which allows the characterisation in solution like the chromatographic determination of the molecular weight.

2. Swelling/Gel Formation

After heating to a temperature higher than 80° C. and subsequent cooling of an aqueous suspension, glucan particles prepared as described above swell and yield a voluminous gel. This gel is stable for several years when it is stored in organic solvents like methanol or acidified water.

3. Stability at High pH-values

Glucan particles as described are much more stable at high pH values (>pH 10) as compared to conventional glucans, which are solubilized at high pH values.

4. Molecular Weight

Glucan particles as described are insoluble in water and in common organic solvents. Therefore, for the determination of the molecular weight it is necessary to solubilize the glucan particles by an as much as possible mild derivatization method. For example, carboxymethylation under common, only slightly degrading conditions (alkaline isopropanol, chloroacetic acid) yields a water soluble product. Analysis of the product by FFFF (flow field-flow-fractionation) resulted in $M_w$=880000 and $M_n$=581000 (Comparison: Mw=35300 and $M_n$=35000 for underivatized glucan D. L Williams, H A. Pretus, H E. Ensley, I. W. Browder, Carbohydr. Res. 253, 293 (1994)); Mw=110000 and $M_n$=25000 for glucan phosphate (D. L. Williams, R. B. McNamee, E. L., Jones, H. A. Pretus, H. E. Ensley, I. W. Browder, N. R. Di Luzio, Carbohydr Res. 219, 203 (1991)).

5. Microscopy

Figure 2:
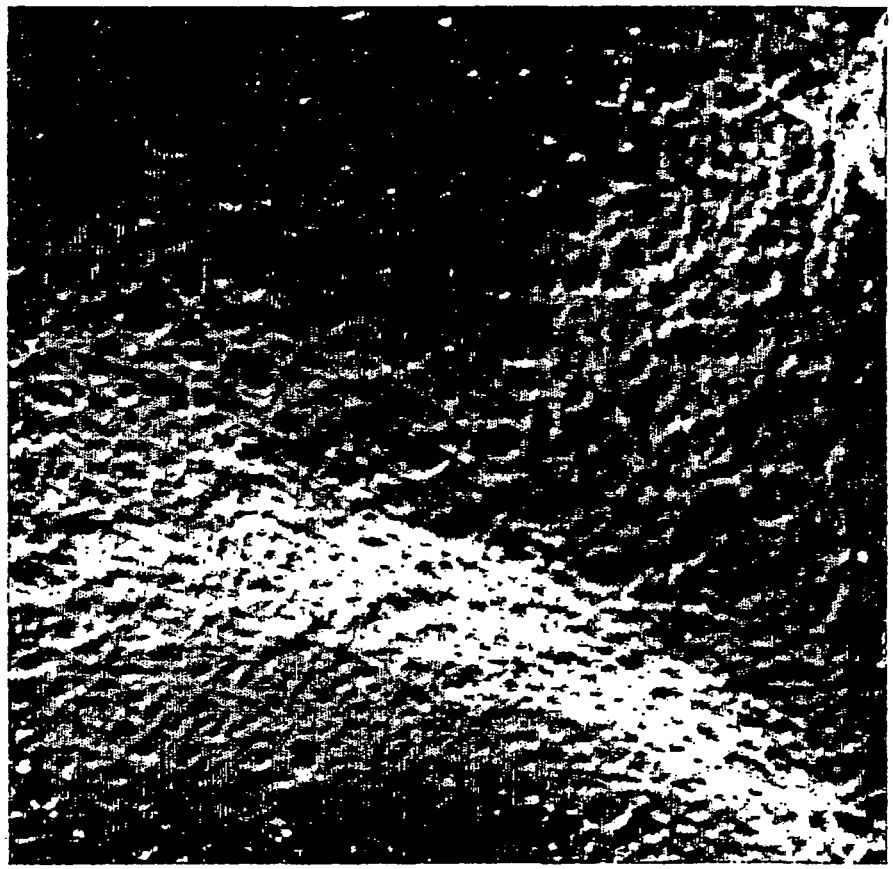
FIG. 2 presents an electron micrograph of the surface of a glucan particle according to example 2b, acetone treated sample; side length 1.08 µm.
Figure 3:
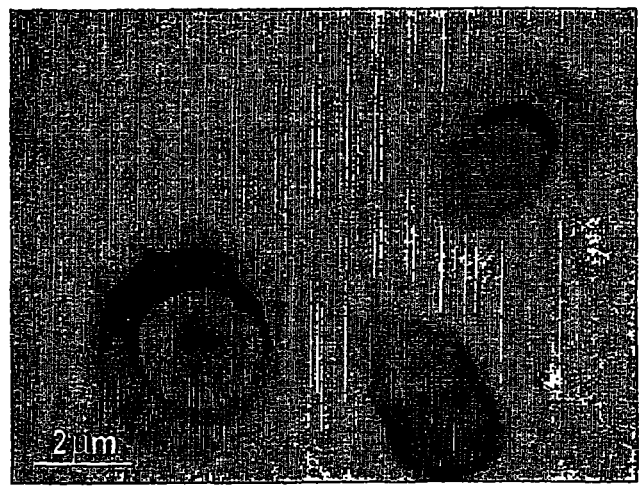
FIG. 3 presents a confocal fluorescence microscopy image of lipid-containing glucan particles according to Example 2b.
Figure 4:
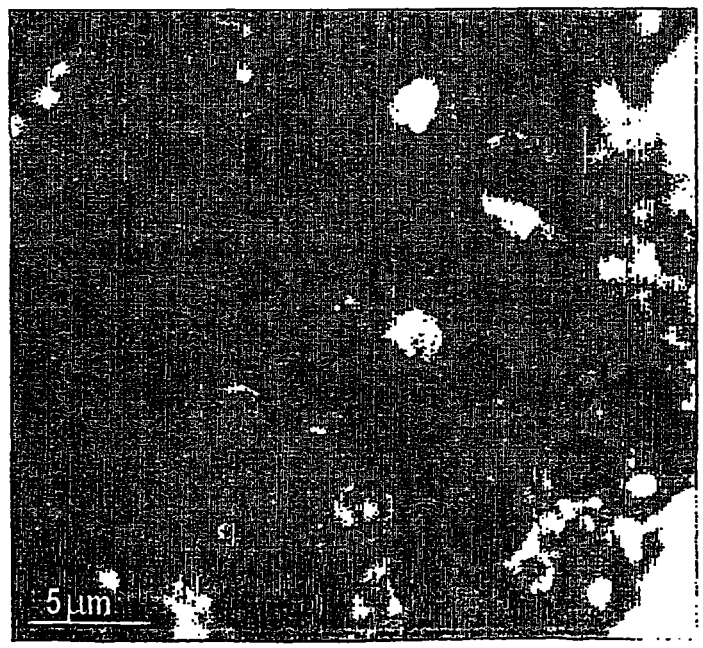
FIG. 4 presents confocal fluorescence microscopy image after cross-linking and carboxymethylation of acetone-treated glucan particles according to Example 2b.

Microscopy techniques were used to show the structural features of the glucan isolated according to the invention. Electronmicrography shows the porous surface (FIG. 2) and confocal fluorescence microscopy demonstrates the shape and size of the glucan particles (FIGS. 3 and 4).

6. Particle Size Distribution

Figure 5:
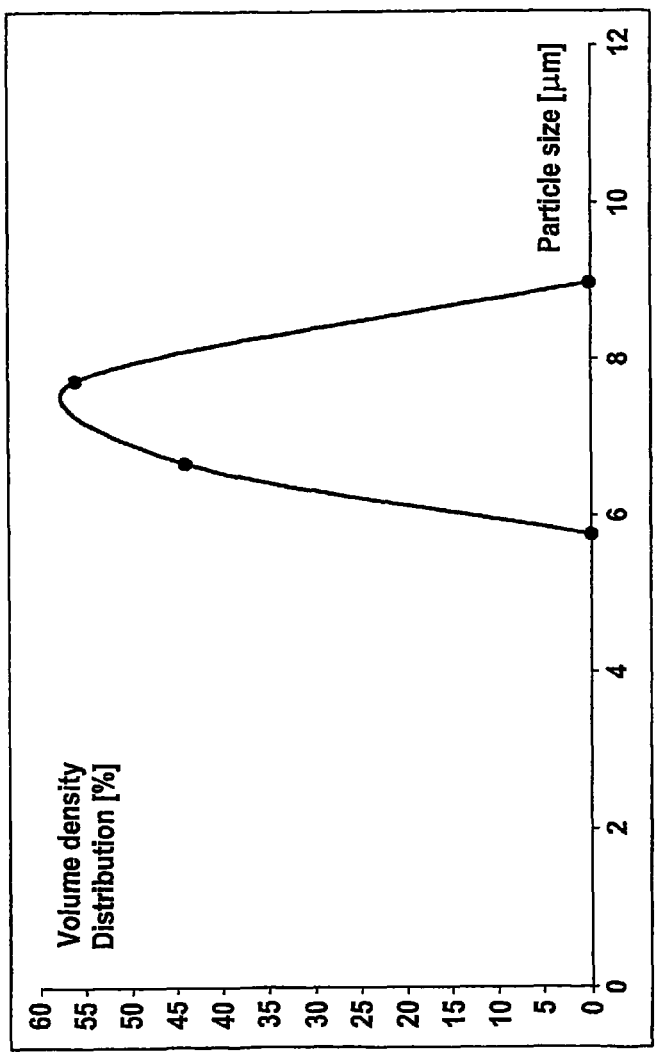
FIG. 5 presents a particle size distribution of acetone-treated glucan particles according to Example 2b in water.

By means of light scattering a particle size distribution has been determined (FIG. 5).

Determined particle sizes of the prepared new glucan are in a size range of 0.1 to 25 micrometers. Most of the particles show particle sizes in the range of 0.5 to 15 micrometers, especially in the range of 2 to 10 micrometers 7. Determination of Purity For the determination of the purity of distinct fractions of glucan particles, the elemental composition of the main possible components are used:
Pure glutton: C 44.A5 H 6.22
Pure mannan: C44.45 H 6.22
Triglycerides: C-72 H-14
Protein: C-53 H-6.5 N-17

In summary the preparation of glucan particles is characterised by the following steps:

a) Preparation of protein- and lipid-containing glucan particles from glucan containing starting material, in particular from yeast cell walls by heating an aqueous suspension of yeast cell walls for several hours at elevated temperature above the boiling point of water under elevated pressure.

b) Preparation of lipid-containing glucan particles by treating particles from step a with proteases c) Preparation of glucan particles by treating lipid-containing glucan particles from step b) with lipases or preparation of glucan particles by combining steps b and c or steps c and b respectively or in variation of the lipase treatment: solvent extraction, e.g. with acetone.

Therefore, the described products are useful in a wide range of applications: as carrier in cosmetic or pharmaceutical formulations, as additive for feed and food, as adsorbent for toxic environmental compounds, as active material in chromatography or for immobilisation of substances in different fields of application, such as biotechnology as well as in chemical processing. Glucan particles according to the invention may be used for the formulation of products needed in agriculture in particular in crop protection, since these products have a potential as health promoting agent for animals and humans. Glucan particles cording to the invention are also useful for the preparation of pharmaceutical formulations with immune system activating properties as well as for formulations with anti tumor activity or for administration in combination with chemotherapy or dialysis. Since materials prepared according to the present invention are able to stimulate the activity of the immune system, these glucan particles can be used to prepare pharmaceutical formulations to improve the host-defences to bacterial or virus infections as well as such with glucose regulating effect or with improving influence on cardiovascular diseases, in treatment of HIV, and other auto immune conditions like arthritis, lupus, allergic asthma, multiple sclerosis and so on. They are also useful for the preparation of pharmaceutical formulations with prophylactic activity against diseases of age and such with cholesterol reduction activity.

As health promoting agent for animals and, humans glucan particles of the present invention may be contained in food supplement or dietary compositions.

They can be taken or administered to warm blooded mammals in need thereof in various forms such as dried powder mixed with liquid, as a pill, tablet or capsule as part of other formulations for a regulated diet. In addition to the inventive compounds, a variety of fillers, flavouring agents, binders, minerals and vitamins as well as typical adjuvants used in the art can be used for the preparation of the administration forms. Sorbitol as a sweetener can be mentioned as well as dicalcium phosphate and magnesium stearate as mineral agents are also suitable.

Glucan particles according to the invention, that can be isolated as a powder, may be used as food or dietary supplement, which can be used in conjunction with a dietary plan.

In preparing the dietary products of the invention, a dry granulation technique may be used that is well understood in the art. Typical equipment used is a roll compactor known as a "Chilsonator" made by the Fitzpatrick Company. The Chilsonator densities the blended powder by passing the powder between high pressure rollers, which compresses the powder and removes the air. The densified material is reduced to a uniform granule size and can be compressed into tablets after addition of a lubricant in accordance with conventional practice. The blending of the dehydrated powdered glucans and other ingredients and conventional excipients can be carried out with a powder blending machine. This equipment is well known in the art.

The food supplement, dietary and pharmaceutical compositions of this invention will contain glucan particles, which can be isolated according to the described process, together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of tablets, pills, capsules, powders, sustained-release formulations and the like. Suitable pharmaceutical carriers are described in "Remington's pharmaceutical Sciences" by E. W. Martin. Such compositions will contain an effective therapeutic amount of the active ingredients together with a suitable amount of carrier so as to provide the form for proper administration to the host. These formulations may also contain mannoprotein as such or in combination with glucan particles according to this invention.

The compositions of this invention can further include a filler, flavouring agent, binder, mineral, vitamin as mixtures thereof. Tablets can be coated with a film mad/or colour layer for protection mad colour as is known in the art. These additives are conventional components of dietary products.

It has also been found, that the isolated mannoprotein from the hot water treatment can be used in the same rammer as the inventive glucan particles for food or pharmaceutical applications. Most advantageously such formulations are prepared using the inventive glucan particles in combination with this mannoprotein.

Without further elaboration, it is believed that one skilled in the art can, using the g description, utilise the present invention to its fullest extent. The preferred specific embodiments and examples of the following are, therefore, to be construed as merely illustrative, limitative of the disclosure in may way whatsoever The entire disclosures of all applications, patents, and publications cited above and below are hereby incorporated by reference.

Example 1

Preparation of Glucan Particles a) Hot Water Treatment

Dry yeast cell walls (1.3 kg) were suspended in water (8.7 l) and the suspension was adjusted to pH 7 by adding an aqueous sodium hydroxide solution (30% w/w). The suspension was heated to 120° C. and stirred for 5 h. After cooling, the suspension was diluted with water (7.3 l) and centrifuged (20 mm, 4000 rpm). The supernatant was removed and the sediment resuspended in water (total weight: 17 kg). After centrifugation and removal of the supernatant, the sediment was ready for the next step.

For analytical purposes, an aliquot of the sediment was several times washed with water and centrifuged until the supernatant was colourless and clear and then freeze-dried yielding a pale yellow powder.
Yield: 63.6%
Protein content: 7.9%
Lipid content: 16.3%
Elemental analysis: C, 50.5%; H, 7.5%; N, 3.3% b) Protease Treatment

The washed sediment from step a) was resuspended in water to a final volume of 10 l. Then the suspension was heated to 45° C. and adjusted to pH 10.5 by adding an aqueous sodium hydroxide solution (30% w/w). Savinase (7.5 ml) was added at t=0, 1.5 and 3 h. After an overall duration of 5 h, the suspension was neutralised with acetic acid (100%) and centrifuged (30 mm, 4000 rpm). After removal of the supernatant, the sediment was ready for the next step.

For analytical purposes, an aliquot of the sediment was several times washed with water and centrifuged until the supernatant was colourless and clear and then freeze-dried yielding a pale yellow powder.
Yield (referring to starting material): 31.6%
Protein content: 3.5%
Lipid content: 17.3%
Elemental analysis: C49.7%; H7.5%; N1.2% c) Solvent Treatment

The moist sediment from step b) was treated with a large excess of acetone and filtered. The residue was washed several times with acetone until the filtrate was colourless and clear and then dried yielding a pale yellow powder.
Yield (referring to starting material): 25.7%
Protein content: 42%
Elemental analysis: C, 46.2%; H, 6.7%; N, 1.6%

Preparation of Mannoprotein

The first supernatant from step a) was added to ethanol (95%) under stirring until the water content reached 30%. The mixture was stored over night at 5° C. leading to a precipitate. The precipitate was filtered, washed several times with ethanol and then dried yielding a white powder.
Yield (referring to starting material): 14.0%
Protein content: 15.4%
Elemental analysis: C, 43.1%; H, 6.2%; N3.7%

Figure 6:
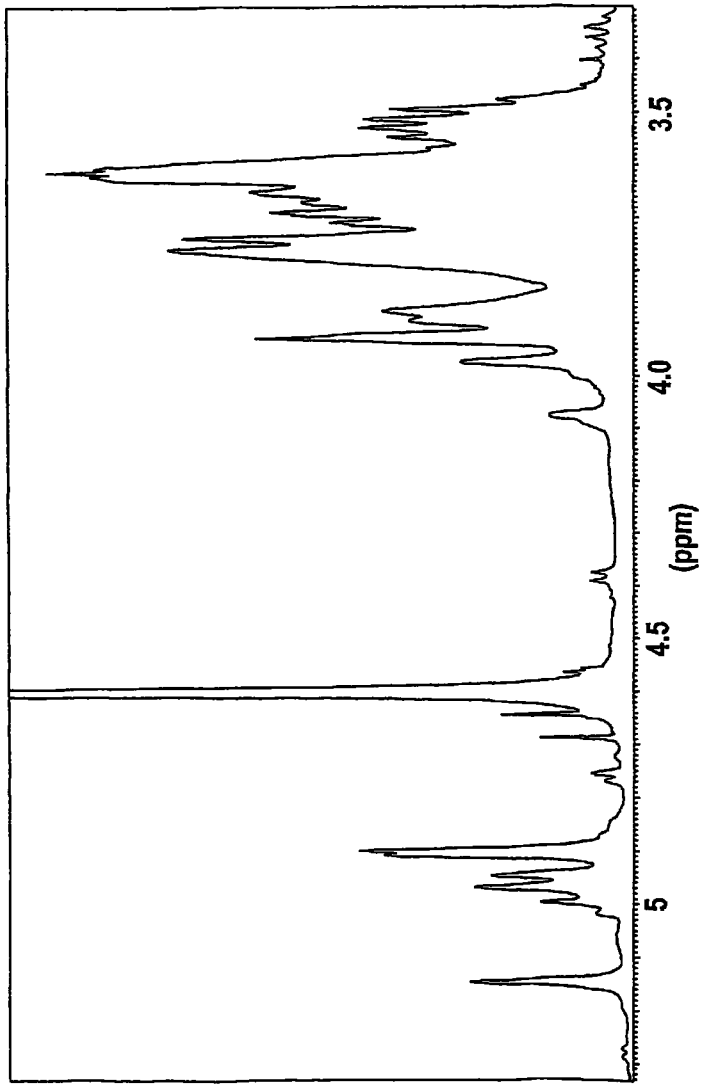
FIG. 6 presents a $^1$H NMR spectrum of mannoprotein according to Example 1 in $D_2O$.
Figure 7:
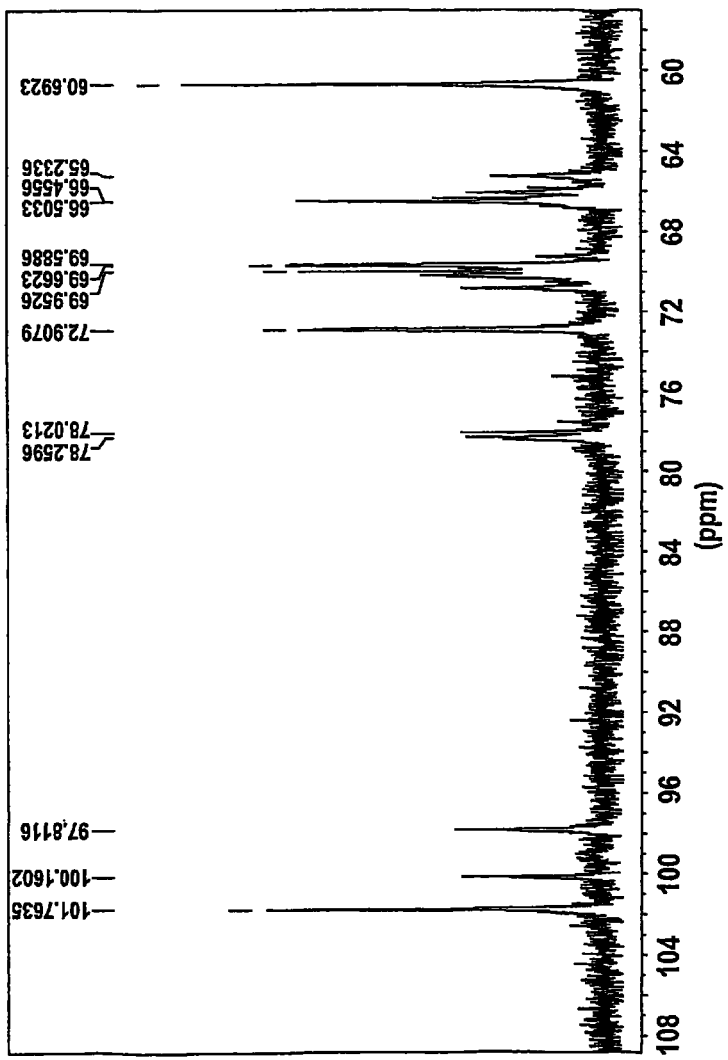
FIG. 7 presents a $^{13}$C NMR spectrum of mannoprotein according to Example 1 in $D_2O$.

$^1$H and $^{13}$C NMR spectra are shown in FIGS. 6 and 7.

Example 2

Preparation of Glucan Particles on Pilot Scale a) Hot Water Treatment 150 kg yeast cell walls, washed free of water-soluble components, were suspended in 850 l of tap water, and the pH was adjusted to 7. The suspension was heated to 125° C. under stirring adapting the stirrer speed accordingly in order to prevent heat gradients and especially local overheating, which leads to gelation. The overpressure amounted to approximately 1.3 bar. After 5 h the suspension was cooled to 45° C. Vacuum formation was prevented during cooling by opening an air inlet valve equipped with a sterile filter~The lipid protein containing glucan particles were separated by centrifugation (Westfalia SB 07 centrifuge) and washed twice with water. The washed sediment was used in the next step.

b) Protease Treatment

Lipid and protein containing glucan particles were resuspended in a total volume of 470 l of tap water with a temperature of 45° C. The pH was adjusted to 10.5 with a 30%-NaOH solution. Then 3.5 l of proteolytic enzyme solution SAVINASE 16.0 L EX (Novo) containing 0.4 l of SAVINASE adapted detergent solution (according to manufacturer specifications) were added with stirring. After 3 h the pH dropped to 9 5 indicating protein hydrolysis. Therefore, the pH was readjusted step-wise to 10.5 and incubation was carried on until pH remained constant (~2 h). After neutralisation lipid containing (protein free) glucan particles were harvested by centrifugation and washed twice with water. The washed sediment was used in the next step.

For analytical purposes, a small amount of the sediment was treated with an excess of acetone and filtered. The residue was washed three times with acetone and subsequently dried.
Elemental analysis: C, 45.1%; H, 6.3%, N; 12%

Figure 8:
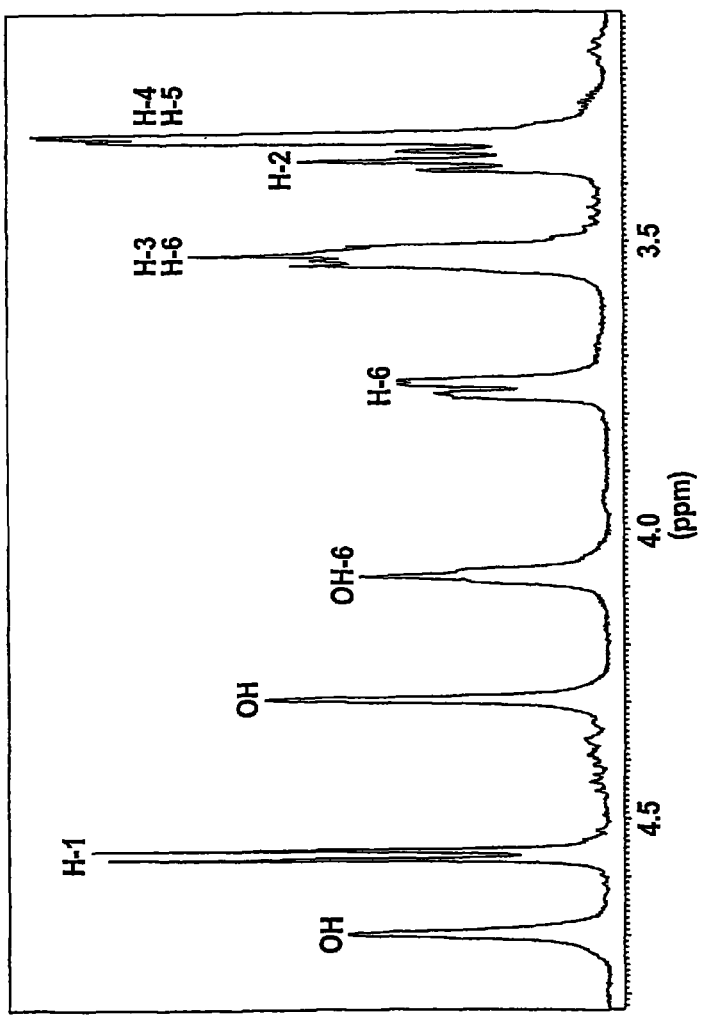
FIG. 8 presents a $^1$H NMR spectrum of acetone-treated glucan particles according to Example 2b in $D_6$-DMSO.
Figure 9:
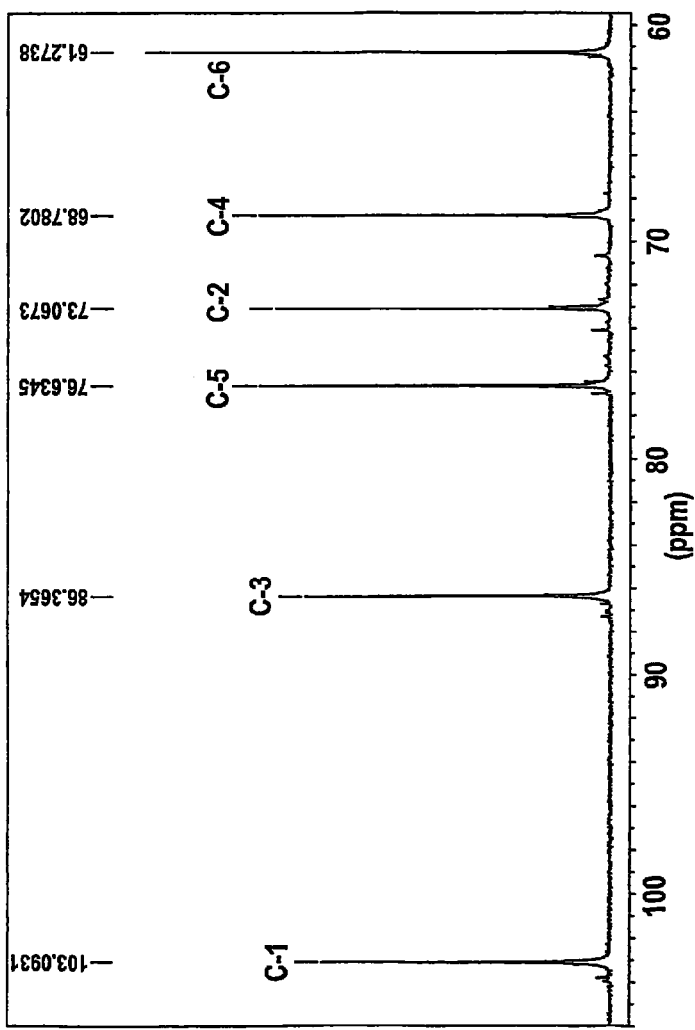
FIG. 9 presents a $^{13}$C NMR spectrum of acetone-treated glucan particles according to Example 2b in $D_6$-DMSO.

$^1$H and $^{13}$NMR spectra including the assignment of the signals are shown in FIGS. 8 and 9.

c) Lipase Treatment 10 l of the 470 l hot water extracted, protease treated cell wall suspension were further treated with 100 g of LIPOLASE 100 L EX (Novo) containing 4 ml of LIPOLASE adapted detergent solution (according to manufacturer specifications) at 45° C. and pH 10.5 with stirring for three hours. The (protein and lipid free) glucan particles were harvested by centrifugation, washed twice and lyophilised.

Example 3

Variation of Protease Treatment

Yeast cell walls were suspended in water to a final concentration of 11%. The pH was adjusted to 10.5 by adding an aqueous sodium hydroxide solution (30% wlw). The suspension was heated to 50° C. under stirring and the reaction was started by the addition of Savinase (3 ml/l suspension). As a standard procedure the addition of equal amounts of Savinase was repeated after 1 and 3 h, respectively. Total incubation time was 4 h. The pH was kept at 10.5 throughout the incubation by addition of adequate amounts of sodium hydroxide whenever necessary. Finally the suspension was neutralised by adding acetic acid and the product was isolated by centrifugation (20 min, 5000 rpm). The sediment was washed twice with water and fats were removed by acetone treatment of the moist sediment as described in Example 1. After drying the protein content was analysed and the results are summarised in table 1.

TABLE 1

Lipid extraction of dry cell walls.

| Variation of protease treatment | Protein content [%] |
|---|---|
| Standard procedure | 4.5 |
| Additional washing after every protease step | |
| Overnight incubation after third addition of Savinase | 2.4 |
| Additional treatment with 2% SDS overnight after third Savinase step | 1.2 |

Example 4

Lipid Extraction of Dry Cell Walls with Organic Solvents 10 g of dry cell walls (named A containing 16.1% of lipids and B containing 13.4% of lipids) were suspended in 200 ml of an organic solvent. The suspension was heated at reflux for 2 h. After cooling to 40° C., the mixture was filtered. The residue was washed two times with 30 ml of warmed solvent and subsequently dried yielding a colourless or slightly yellowish powder. The combined filtrates were evaporated yielding brownish oil Table 2 summarises the results of the extractions.

TABLE 2

Lipid extraction of dry cell walls.

| Solvent | cell walls | lipid content (%) | extracted lipids content (%) | total (%) |
|---|---|---|---|---|
| n-Hexane/methanol 4:1 (v/v) | A | 16.1 | 15.5 | 96 |
| Ethanol (techn.) | " | " | 14.3 | 89 |
| Methanol (abs.) | " | " | 14.7 | 91 |
| Ethanol (techn.) | B | 13.4 | 10.9 | 81 |
| Methanol (abs.) | " | " | 10.9 | 81 |

Example 5

Lipid Extraction of Spray-dried Lipid Containing Glucan Particles with Organic Solvents 10 g of spray-dried lipid containing glucan particles (from Example 1)

TABLE 3

Lipid extraction of spray-dried lipid containing glucan particles

| Solvent | extracted lipids content (%) | total (%) |
|---|---|---|
| n-Hexane/methanol 4:1 (v/v) | 28 | 100 |
| n-Hexane | 2 | 7 |
| n-Hexane/isopropanol 4:1 (v/v) | 5 | 17 |
| Isopropanol | 12 | 43 |
| Acetone (tech.) | 10 | 37 |
| Acetone/$H_2O$ 4:1 (v/v) | 27 | 96 |
| Ethanol (abs.) | 27 | 96 |
| Ethanol (tech.) | 27.5 | 98 |
| Methanol (abs.) | 28 | 100 |

Example 6

Adsorption by Glucan Particles 30-70 mg of glucan particles were homogeneously suspended in 100 ml of distilled water. The compound of interest was added as stock solution to the glucan suspension. After stirring this mixture for some time the glucan particles were removed from the suspension by centrifugation. The concentration of the compound in the supernatant was determined and the amount of the compound adsorbed by the glucan particles was calculated from the difference between the starting and the end concentration of the compound.

Different classes of compounds, like proteins (e.g. 17 mg of lysozyme bound per g of glucan particles, 43 mg of myoglobine bound per g of glucan particles), flavours (e.g. 4 mg of eugenol bound per g of glucanparticles) or toxins (e.g. 2.5 mg zearalenone bound per g of glucan particles), were absorbed by the glucan particles

Example 7

Glucan Particles as Carrier

Retinal (370 mg) was melted and glucan particles (3.0 g) were added gradually within 10 minutes under stirring at 75° C. Stirring was continued for 10 minutes. After cooling a yellow, free flowing powder was obtained.

What is claimed is:

1. Activated yeast cell walls, wherein the activated yeast cell walls are activated by a process comprising a sequential treatment of yeast cell walls comprising:
   a) a treatment with heat above the boiling point of water;
   b) a treatment with a protease DB; and
   c) a treatment with a lipase,
   with the order of steps being free.

2. Activated yeast cell walls of claim 1, wherein the activated yeast cell walls are microparticles, wherein the chemical and structural backbone of said microparticles is (1-3; 1-6) beta-D-glucan.

3. Process for removing compounds from a solution, comprising suspending less than 1% (weight per volume) of activated yeast cell walls of claim 2 in said solution, adsorbing said compounds to said activated yeast cell walls, and removing the activated yeast cell walls containing the adsorbed compounds.

4. The process of claim 3 wherein said compounds are mycotoxins.

5. A process for loading compounds onto activated yeast cell walls of claim 2, wherein said compounds are liquid or heat-liquefied, comprising adding said compounds, under stirring, to a maximum hundred fold amount of particles (weight by weight).

6. Process for loading compounds onto activated yeast cell walls according to claim 2, comprising providing a suspension of said activated yeast cell walls, adding to said suspension of activated yeast cell walls the compounds at a concentration of at least 1% (weight per weight) of that of the activated yeast cell walls, and recovering said activated yeast cell walls.

7. The process of claim 6, further comprising dissolving said compounds in a water-miscible solvent prior to adding the compounds to said suspension.

8. A process for loading water-immiscible compounds onto activated yeast cell walls of claim 2, comprising adding said activated yeast cell walls to a solvent solution of said water-immiscible compounds at a maximum hundred fold concentration (weight per weight) of said water-immiscible compounds and subsequently recovering the activated yeast cell walls with the compounds by evaporating said solvent.

9. The activated yeast cell walls of claim 2, produced by the process of activating unicellular organisms of plant material that contain glucan or glucan equivalent polysacchardies.

10. The process of claim 3, further comprising removing the activated yeast cell walls by a method selected from the group consisting of centrifugation and filtration.

11. The process of claim 6, further comprising recovering said activated yeast cell walls by a method selected from the group consisting of drying and centrifugation.

12. The process of claim 5, wherein said compounds are selected from the group consisting of water extracts of plants or plant parts, non-aqueous extracts of plants or plant parts, catalytically active compounds, human health promoting compounds, animal health promoting compounds, pharmaceutically active compounds, and cosmetically active compounds.

13. The process of claim 6, wherein said compounds are selected from the group consisting of water extracts of plants or plant parts, non-aqueous extracts of plants or plant parts, catalytically active compounds, human health promoting compounds, animal health promoting compounds, pharmaceutically active compounds, and cosmetically active compounds.

14. The process of claim 7, wherein said compounds are selected from the group consisting of water extracts of plants or plant parts, non-aqueous extracts of plants or plant parts, catalytically active compounds, human health promoting compounds, animal health promoting compounds, pharmaceutically active compounds, and cosmetically active compounds.

15. Activated yeast cell walls of claim 1, wherein the activated yeast cell walls have a particle size of 0.1 to 25 micrometers.

16. Activated yeast cell walls of claim 1, wherein the activated yeast cell walls comprise activated pores.

17. A process of preparing the activated yeast cell walls according to claim 1, comprising separating the yeast cell walls from the bound mannoprotein at a pH of 6 to 8.

18. A process of preparing the activated yeast cell walls according to claim 1, comprising separating the yeast cell walls from the bound mannoprotein at a pH of 6.5 to 7.5.

19. Activated yeast cell wall of claim 1, wherein the activated yeast cell walls comprise a native porous structure.

20. A process of preparing activated yeast cell walls comprising a sequential treatment of yeast cell walls, the process comprising:
   a) a treatment with heat above the boiling point of water;
   b) a treatment with a protease; and
   c) a treatment with a lipase,
   with the order of steps being free.

21. The process of claim 20, wherein the process consists of the steps a), b) and c).

* * * * *